United States Patent
Sundsdal (10) Patent No.: US 11,986,174 B2
(45) Date of Patent: May 21, 2024

(54) MEDICAL INSTRUMENT GRIP DEVICE

(71) Applicant: Tannlege E. Sundsdal Auensen AS, Oslo (NO)

(72) Inventor: Elisabeth Sundsdal, Oslo (NO)

(73) Assignee: Tannlege E. Sundsdal Auensen AS, Oslo (NO)

( * ) Notice: Subject to any disclaimer, the term of this patent is extended or adjusted under 35 U.S.C. 154(b) by 707 days.

(21) Appl. No.: 15/775,659

(22) PCT Filed: Nov. 10, 2016

(86) PCT No.: PCT/EP2016/077205
§ 371 (c)(1),
(2) Date: May 11, 2018

(87) PCT Pub. No.: WO2017/081118
PCT Pub. Date: May 18, 2017

(65) Prior Publication Data
US 2018/0344302 A1    Dec. 6, 2018

(30) Foreign Application Priority Data

Nov. 12, 2015  (NO) .................................. 20151545

(51) Int. Cl.
*A61C 1/16* (2006.01)
*A61B 1/24* (2006.01)
(Continued)

(52) U.S. Cl.
CPC ............... *A61B 17/00* (2013.01); *A61B 1/24* (2013.01); *A61C 1/16* (2013.01); *A61C 3/00* (2013.01);
(Continued)

(58) Field of Classification Search
CPC ....................................................... A61C 1/16
See application file for complete search history.

(56) References Cited

U.S. PATENT DOCUMENTS 2,073,137 A * 3/1937 Bimrose .................. A61C 1/16
15/246
4,646,722 A * 3/1987 Silverstein ......... A61B 1/00142
600/122
(Continued)

FOREIGN PATENT DOCUMENTS

DE    202010006836 U1    9/2011
FR         2882249 A1    8/2006
WO     2008/111748 A1    9/2008

OTHER PUBLICATIONS

International Search Report issued in PCT/EP2016/077205 dated Feb. 1, 2017 (4 pages).
(Continued)

*Primary Examiner* — Ralph A Lewis
(74) *Attorney, Agent, or Firm* — Osha Bergman Watanabe & Burton LLP (57) ABSTRACT

A medical instrument grip device consisting of an open tubular element of elastic material for an elongated medical instrument comprises an elongated element having a gripping area and a head element being attached to one of the ends of the elongated element. The tubular element is open in both longitudinal ends and is configured to switch between a rolled up state and a fully unrolled state. Further, the tubular element is configured such that the head element may be forced through the inner opening of the stretched tubular element being in its rolled up state and to create a tight fit around the gripping area when being in its unrolled state.

19 Claims, 4 Drawing Sheets (51) Int. Cl.
    *A61B 17/00*     (2006.01)
    *A61C 3/00*     (2006.01)

(52) U.S. Cl.
    CPC ............... *A61B 2017/00429* (2013.01); *A61B 2017/00862* (2013.01); *A61C 2202/00* (2013.01)

(56) References Cited

U.S. PATENT DOCUMENTS

| | | | |
|---|---|---|---|
| 4,741,326 A * | 5/1988 | Sidall | A61B 1/00142 |
| | | | 600/125 |
| 4,789,336 A | 12/1988 | Lewis | |
| 5,228,851 A * | 7/1993 | Burton | A61C 1/16 |
| | | | 206/306 |
| 5,267,860 A * | 12/1993 | Ingram, Jr. | A61C 1/16 |
| | | | 433/115 |
| 5,407,354 A | 4/1995 | Fife | |
| 6,305,937 B1 | 10/2001 | Williams | |
| 6,443,729 B1 * | 9/2002 | Watson | A61B 1/253 |
| | | | 433/116 |
| 2007/0224571 A1 * | 9/2007 | Watson | A61B 1/253 |
| | | | 433/31 |
| 2008/0213721 A1 | 9/2008 | Euvrard et al. | |
| 2010/0063359 A1 * | 3/2010 | Okoniewski | A61B 1/00142 |
| | | | 600/121 |
| 2010/0095487 A1 | 4/2010 | Gitman et al. | |

OTHER PUBLICATIONS

Written Opinion issued in PCT/EP2016/077205 dated Feb. 1, 2017 (6 pages).

Norwegian Search Report issued in U.S. Appl. No. 20/151,545 dated Jun. 12, 2016 (2 pages).

\* cited by examiner

MEDICAL INSTRUMENT GRIP DEVICE

FIELD OF THE INVENTION

The present invention relates to a grip device for medical instruments, especially dental instruments to provide a better grip on the instrument while operating it.

BACKGROUND OF THE INVENTION

The instruments or tools used by dentists or surgeons when operating patients are often small in diameter size at the gripping area, rigid and made of metal. The instruments are therefore often slippery and cold, making them difficult to operate in a precise manner with good control, considering that the user's hand and fingers must maintain a static position over an extended period of time when operating the instrument.

Additionally, it is well known that repetitive motion by the wrist, hand and fingers can lead to adverse medical conditions such as carpal tunnel syndrome (CTS). In the dental and the dental hygiene professions, the extensive use of small finger-gripped tools and instruments results in considerably hand fatigue, which over time may result in long term or permanent injury.

US 2008/0213721 A1 relates to a protective device for dental equipment having a sleeve that has a form of a glove finger being open at only one end. The sleeve is preferably compacted or rolled up externally on itself and can be placed on the distal end of the tool-holder head, its closed end being cut by the tool, and, in the position of use, the sleeve is unrolled on the head and on the hand piece of the tool.

U.S. Pat. No. 6,305,937 B1 discloses a releasably mountable hand grip for dental tools which increases the diameter of the portion of the tool which is grasped. The hand grip is made of soft and non-rigid material with a non-slip textured surface, and which is capable of being sterilized at very high temperatures without damage. The hand grip is mounted by sliding the cylindrical hand grip on to the tool, wherein the tool preferably has a tapered front. The hand grip may optionally be mounted using a lubricant to aid in moving the hand grip over the tool.

US 2007/0224571 A1 discloses a light mirror instrument comprising a protective roll-up sheath to prevent spread of germs and debris, which is attached to the instrument. The one end of the sheath is affixed around the one end of the instrument.

It is thus an object of the present invention to provide a replaceable grip device which easily can be mounted to tapered and non-tapered instruments, straight and contra-angle instruments and instruments having a larger instrument head circumference than the grip circumference. Thus, the grip device of the present invention can be applied to gripping area of many different kinds of instruments such as a dental handpiece with a large head, and dental handpieces comprising a mouth mirror, a sickle probe or the like attached thereto.

Further, the grip device of the present invention does not need a lubricant to ease the application of the grip device on to the instrument, since the device is not supposed to be sliding when rolled on to the instrument.

It is further an object of the present invention to provide a grip device giving the user a better and more comfortable grip on the instrument by making the gripping area of the instrument non slippery, warmer (due to reduced thermal conductivity) and ergonomically better to hold.

A further aim of the present invention is to provide a grip device that is easy to apply and easy to remove in order for the device to be changed after each patient. The present invention is therefore applicable for one-time-use.

Since instruments used in dental treatment, dental hygiene and other medical fields have been widely adopted and are not likely to be replaced, the present invention comprises an improvement in the grip which is suitable for already existing instruments and tools.

RELATED ART DOCUMENTS

[NON-PATENT DOCUMENT 1] "Shore durometer," Wikipedia, The Free Encyclopedia, 17 Mar. 2023. Web address: https://en.wikipedia.org/wiki/Shore_durometer#Durometer_scales.

[NON-PATENT DOCUMENT 2] "Durometer Shore Hardness Scale," Smooth-On. Web address: http://www.smooth-on.com/pdf/durometer_with_logo.pdf or http://www.smooth-on.com/Documents-Durometre/c1351_1370/index.html.

SUMMARY OF THE INVENTION

The present invention is set forth and characterized in the independent claims, while the dependent claims describe other characteristics of the invention.

The present invention is directed to a medical instrument hand grip device suitable for dental treatment/surgery, dental hygiene, medical or non-medical tools or instruments, a method for attaching the medical instrument hand grip device around the gripping area of the instrument and the use of such a hand grip device.

The hand grip device of the present invention is an open tubular element of elastic material for a medical instrument, wherein the instrument comprises an elongated element having a gripping area and a head element being attached to one of the ends of the elongated element.

The tubular element is open in both longitudinal ends and configured to switch between a rolled up state and a fully unrolled state, and further configured such that the head element of the instrument is forced through the inner opening of the tubular element while the tubular element is in its rolled up state and creating a tight fit around the gripping area while the tubular element is in its unrolled state.

According to the present invention, the tubular element is elastic.

The circumference of the tubular element can be of any geometrical shape. Hence, the circumference is said to have a cross sectional circumferential distance which corresponds to the largest cross sectional distance within the tubular element. In the context of the invention, the circumference of the tubular element is to be understood as the circumference of the inside of the tubular element where the head element of the instrument is forced through.

The circumference of the head element has a cross sectional circumferential distance, $d_{head}$, corresponding to the largest cross sectional distance within the head element that is to be forced through the inner opening of the tubular element.

Thus, if the circumferential distance, $d_{head}$, of the head of the instrument is larger than the inner circumference of the tubular element in its relaxed state, the tubular element will be expanded, stretched, while forcing the head element of the instrument through the inner opening of the tubular element.

The ratio between the circumferential distance of the tubular element before stretching, i.e. in a relaxed state, and the circumferential distance of the tubular element after reaching the stretched expanded state when forcing the head element through the inner opening, is between 1:1.05 and 1:10, more preferably between 1:1.1 and 1:5, and even more preferably between 1:1.15 and 1:2. The less the ratio, the less is the risk of the elastic material to break or loose its ability to contract back to its relaxed state after stretching. In order to make a tight fit when unrolled onto the gripping area, the material should have the ability to contract back to its relaxed state, or at least contract enough to allow the tubular element to make a tight fit on to the gripping area.

The onset of the gripping area on the elongated element of the instrument is to be understood as the area on the elongated element wherein the tubular element is placed in its rolled up state. The onset of the gripping area is situated at the one end of the intended gripping area of elongated part of the instrument. In the context of the present invention the onset circumferential distance of the gripping area, $d_{grip}$, of the instrument is said to be the maximum cross sectional circumferential distance of the onset of the gripping area of the instrument wherein the tubular element is placed in its rolled up state prior to being unrolled.

The head element can be of any geometrical shape, but if the head of the instrument has a circular cross section, the circumferential distance, $d_{head}$, corresponds to the diameter of the circular cross section. The same applies for the circumferential distance of the gripping area $d_{grip}$, and the circumferential distance of the tubular element when their cross section has a circular shape.

The tubular element is not limited to comprise a circular inner opening. The tubular element can be shaped or stretched into any suitable shape for the head of the instrument to be forced through the inner opening of the tubular element in its rolled up state.

The tubular element must also be adapted to fit to the gripping area of the instrument. The gripping area is limited to an elongated shape having any kind of suitable geometry for the tubular element to obtain a tight fit thereto.

The tubular element of the present invention can thus be made in a size and shape that is adaptable to the size and shape of the instrument to be used.

The configuration of the hand grip device/tubular element makes it easy to apply on to the tool or instrument. The elasticity of the material of the tubular element allows the tubular element to expand when forcing the head of the instrument through the inner opening of the elastic tubular element and thereafter contract when the tubular element is placed at the onset, of the gripping area.

The ratio between the onset circumferential distance of the gripping area, $d_{grip}$, and the maximum circumferential distance of the head element, $d_{head}$, should be less than 1:5. If the maximum diameter of the head of the instrument is too big, the tubular element will break while forcing the head element of the instrument through the inner opening of the tubular element, and/or the tubular element will not be able to contract sufficiently to make a tight fit when unrolled on to the gripping area of the instrument. Preferably, the ratio $d_{grip}/d_{head}$ is less than 1:2, and even more preferably the ratio is less than 1:1.5.

In one aspect of the present invention the outer surface of the tubular element comprises a tactile pattern to improve the grip compared to a smooth surface.

In another aspect according to the invention, the tubular element comprises a strengthening of the material at at least one of the two longitudinal ends. The strengthening comprises a slightly thicker material when compared to the thickness of the rest of the tubular element, thus making the element stronger, increasing the stability of the tubular element and minimizing the possibility of the tubular element to slide off the instrument during use. Preferably, both longitudinal ends comprises such strengthening of the material.

The thickness of the strengthened part is at least 0.1% thicker than the thickness of the remaining part of the tubular element, preferably at least 0.5% thicker, and even more preferably at least 1% thicker than the remaining part of the tubular element.

The tubular element is made of an elastic material, such as organic or synthetic rubber, which is expandable and contractible. Preferably, the tubular element is selected from one of polychloroprene (neoprene), silicon rubber, acrylonitrile butadiene (nitrile), latex, polyisoprene, polyethylene, latex, polyurethane and mixtures thereof.

In another aspect of the invention, the tubular element comprises a smaller circumference at the one longitudinal end compared to the other longitudinal end, and thereby the element expands in its circumference from the one longitudinal end to the other. In other words, the circumferential distance gradually expands from the one longitudinal end of the tubular element to the other (wedged profile).

In another aspect according to the invention, the tubular element comprises at least one weakened area extending along the longitudinal length of the tubular element, and the tubular element should be tearable. The weakened area may further comprise a thinner elastic tubular material compared to the remaining part of the tubular element. The weakened area may comprise perforations in order to facilitate the tear off procedure when removing the tubular element from the instrument.

In another aspect according to the invention, the tubular element comprises an extruding flange on one of its longitudinal ends. The purpose of the flange is to further ease the tear off procedure by allowing the user to grab the flange by fingers or external tools.

In another aspect of the invention, the tubular element is suitable for one-time-use. Instead of sterilization, the tubular element may be easily removed after being used on a patient, and a new tubular element is easily applied before operating the instrument on a new patient. If the tubular element is torn off after use, it can not be fitted back onto the instrument.

The tubular element can be prepacked in a sterile environment before use. The tubular element is thus applicable without the need of being sterilized before use. After operating the instrument with the tubular element on one patient, the element is torn off the instrument. The instrument is subsequently sterilized, and a new tubular element is attached to the instrument before operating the instrument on the next patient. The tubular element can be prepacked in its rolled up state, ready to be attached to the instrument.

The present invention is particularly suitable for a dental instrument comprising an elongated element having a gripping area and a head element being attached to one of the ends of the elongated element, and an open tubular element attached to the gripping area.

The tubular element can be attached to instruments that comprises a head element having a larger circumferential distance, $d_{head}$, than the onset circumferential distance of the gripping area, $d_{grip}$, of the instrument.

Further, the invention relates to the use of the open tubular element.

The present invention also concerns a method for attaching the open tubular element of an elastic material around a gripping area of an elongated instrument, the tubular element being open in both longitudinal ends,
wherein the elongated instrument comprises an elongated element having a elongated gripping area and a head element being attached to one of the ends of the elongated element,
wherein the method comprises the following steps:
forcing the head element through an inner opening of the tubular element, the tubular element being in a rolled up state, and
placing the rolled up tubular element around the onset of the gripping area, and
unrolling the tubular element around the longitudinal length of at least the gripping area, resulting in a tight fit around the elongated element.

The tubular element according to the present invention can be manufactured in different sizes (i.e. inner circumferential distances, thicknesses and lengths) to comply with the instrument onto which it is to be used.

The term "tight fit" is used herein to describe the contact between the longitudinal element and the tubular element. A tight fit means that the tubular element is kept steady onto the instrument, and thus does not allow the tubular element to slide around or off the instrument. The tight fit is caused by frictional engagement between the elastic material of the tubular element and the material of the instrument, such as for example metal.

The term "rolled up state" is used herein to describe a condition of the elastic tubular element. It can be seen as a state corresponding to the state of a condom before being rolled onto a male organ.

The term "unrolled state" is used to describe another condition of the elastic tubular element. In its unrolled state the tubular element is surrounding at least the gripping area of the instrument, creating a tight fit around the gripping area.

Even if the drawings show that the grip device is attached to a dental hand piece, it should be understood by the person skilled in the art that the grip device can be applied to any kind of medical instrument.

Figure 4:
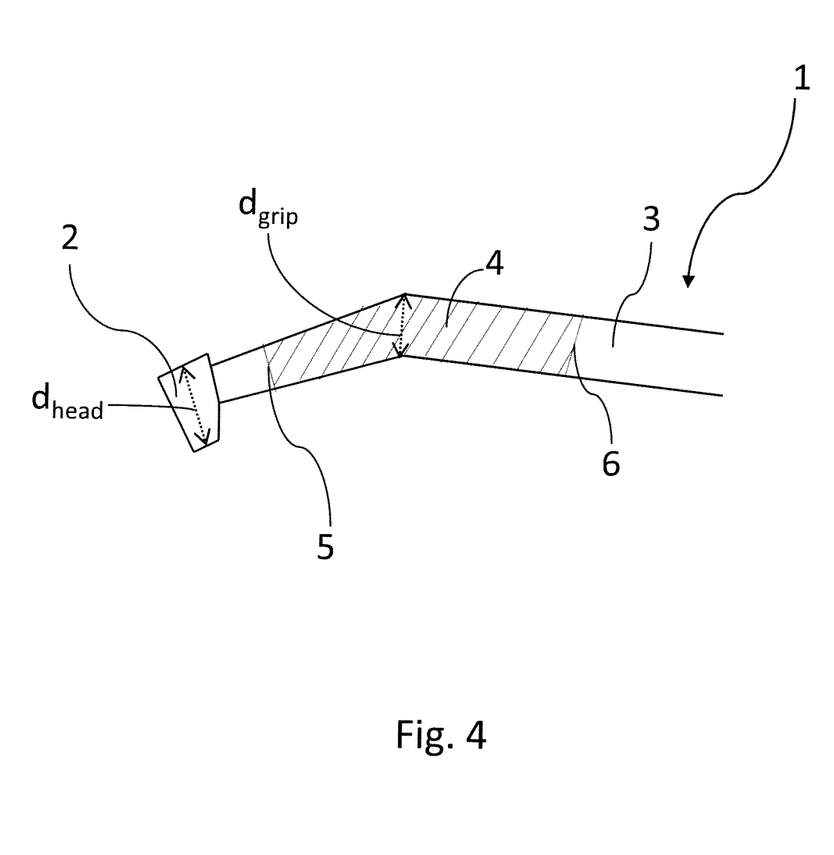
FIG. 4 is also a side view of a prior art dental instrument where the gripping area of the instrument is indicated.

In an alternative solution one may use, the hand grip device is an open tubular element of elastic material suitable for elongated dental instruments, wherein the instruments comprise an elongated element having a gripping area with a maximum diameter $d_{grip}$, and a head element having a maximum diameter $d_{head}$ being attached to one of the ends of the elongated element, see FIG. 4. The tubular element is configured to switch between a rolled up state and a fully unrolled state, and further configured such that the head element may be forced through the inner diameter of the tubular element being in its rolled up state and creating a tight fit around the gripping area while being in its unrolled state.

The configuration of the grip device makes it easy to apply on to the tool or instrument, and since the material of the grip device is of an elastic material, the device can be applied to instruments comprising a head element having a larger maximum diameter than the gripping area of the instrument.

In one aspect the outer surface of the tubular element comprises a tactile pattern to improve the grip compared to a smooth surface.

The tubular element is made of an elastic material, such as organic or synthetic rubber, which is expandable and contractible, thus enabling the material to expand when forcing the head of the instrument through the inner diameter of the elastic material and thereafter contract when the material is placed at the one end of the gripping area and unrolled on to the gripping area.

The tubular element may comprise a smaller diameter at the one longitudinal end compared to the other longitudinal end and thereby the element expands in its diameter from the one longitudinal end to the other.

The tubular element may also comprise at least one weakened area along the longitudinal length of the tubular element and the tubular element should be tearable. The weakened area may further comprise a thinner elastic tubular material compared to the remaining part of the tubular element. The weakened area may comprise perforations, to make it even easier to tear off when removing the tubular element from the instrument.

The tubular element may further comprise an extruding flange on one of its longitudinal ends, making it easier to tear off.

The tubular element is suitable for one-time-use. It is therefore easily removed instead of sterilized after being used on one patient and a new tubular element is easily applied before using the instrument on a new patient. If the grip device is torn off after use, it can not be fitted back on to the instrument.

The tubular element is pre-packed in a sterile environment before use. The tubular element is therefore applicable without the need of being sterilized before use. After the use of the tubular element on one patient, the element is torn off the instrument, and after sterilizing the instrument a new tubular element is attached to the instrument before using the instrument on the next patient. The grip device should be pre-packed in its rolled up state, ready to be attached to the instrument. The instrument is particularly related to a dental instrument comprising an elongated element having a gripping area with a maximum diameter $d_{grip}$, and a head element having a maximum diameter $d_{head}$ being attached to one of the ends of the elongated element, and an open tubular element attached to the gripping area. The open tubular element can be used on medical instruments.

For attaching the open tubular element of an elastic material around a gripping area of an elongated instrument, the tubular element being open in both longitudinal ends, wherein the elongated instrument comprises an elongated element having a gripping area with a maximum diameter $d_{grip}$, and a head element having a maximum diameter $d_{head}$ being attached to one of the ends of the elongated element, the method comprises the following steps:
forcing the head element through the tubular element, the tubular element being in a rolled up state, and
placing the rolled up tubular element around the onset of the gripping area, and
unrolling the tubular element around the longitudinal length of at least the gripping area, resulting in a tight fit around the elongated element.

Even if the drawing 5 shows that the grip device is attached to a dental hand piece, it should be understood by the person skilled in the art that the grip device can be applied to any kind of instrument, as long as the diameter of the grip device is adapted to the size of the instrument to which it is applied.

In the following description, numerous specific details are introduced to provide a thorough understanding of embodiments of the claimed tubular element and the method. One skilled in the relevant art, however, will recognize that these embodiments can be practiced without one or more of the specific details, or with other components etc. In other instances, well-known structures or operations are not shown, or are not described in detail, to avoid obscuring aspects of the disclosed embodiments.

DETAILED DESCRIPTION OF THE INVENTION

Figure 1:
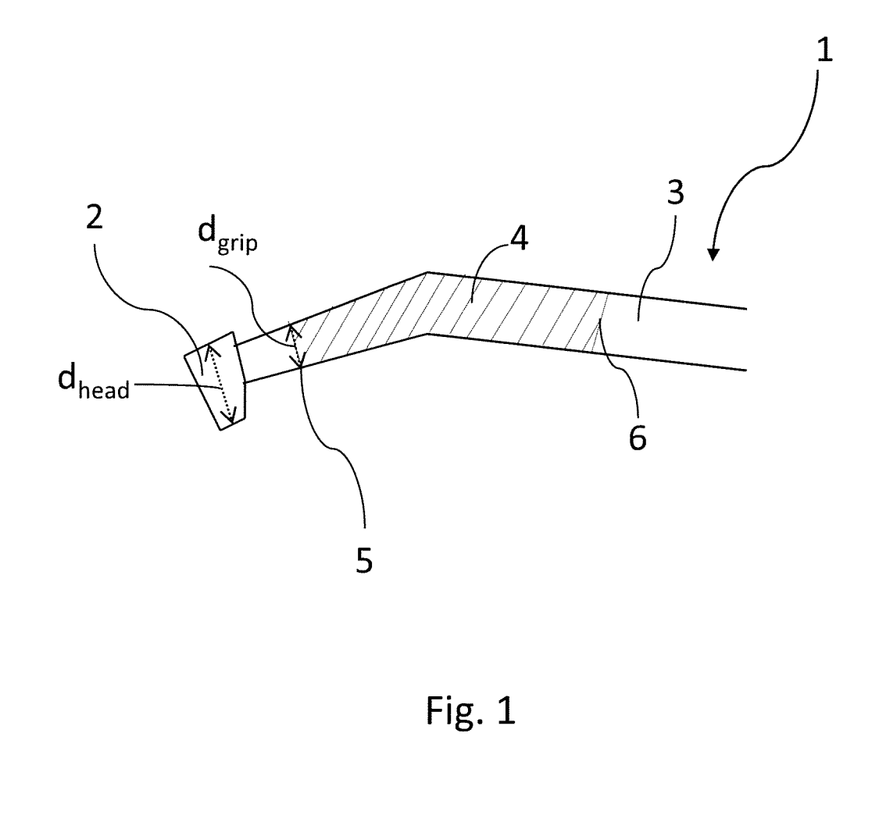
FIG. 1 is a side view of a prior art dental instrument where the gripping area of the instrument is indicated.

FIG. 1 illustrates a prior art dental instrument 1 to which the grip device 7 according to the present invention can be attached. The instrument 1 is normally made of a metal such as stainless steel. The head element 2 of the instrument 1 has in the specific embodiment shown in FIG. 1 a larger circumferential distance, $d_{head}$, compared to the onset 5 circumferential distance, $d_{grip}$, of the gripping area 4.

Figure 2:
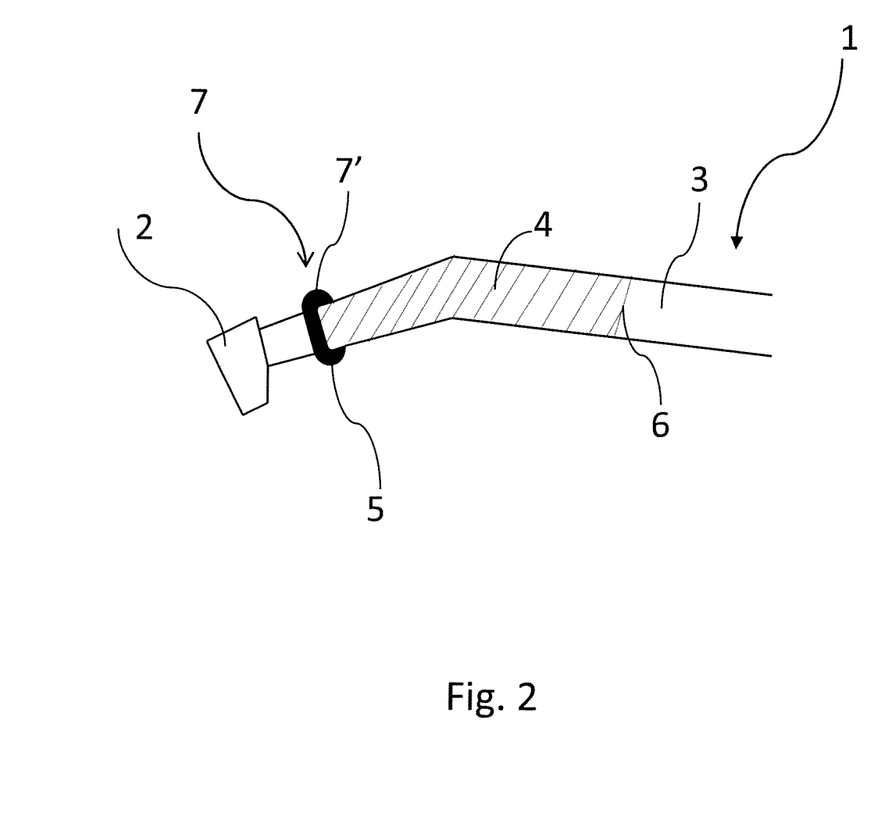
FIG. 2 is a side view of a dental instrument in accordance with FIG. 1, wherein the inventive elastic tubular element is in its rolled up state placed around the onset of the gripping area.

FIG. 2 illustrates the grip device consisting of an open, elongated tubular element 7 in a rolled up state 7' attached around the onset 5 of the gripping area 4 of the instrument 1.

The open elongated tubular element 7 is made of elastic material. The tubular element 7 is in its rolled up state 7' before and during assembly to the gripping area of the instrument 1. The manufacturing of the tubular element 7 using elastic material means that it can be expanded in order to force the head element 2 of the instrument 1 through the inner opening of the tubular element 7 in its rolled up state 7'. After the head element 2 is forced through the inner opening of the tubular element 7 in its rolled up state 7', the elastic material contracts back towards its original circumference. The term "original circumference" is hereinafter defined as the circumference of the element before it was expanded, the relaxed state. The elasticity of the elastic material is thus particularly important when the circumferential distance, $d_{head}$, of the head element 2 is larger than the onset 5 circumferential distance, $d_{grip}$, of the gripping area 4 in order to create a tight fit between the instrument 1 and the tubular element 7.

Figure 3:
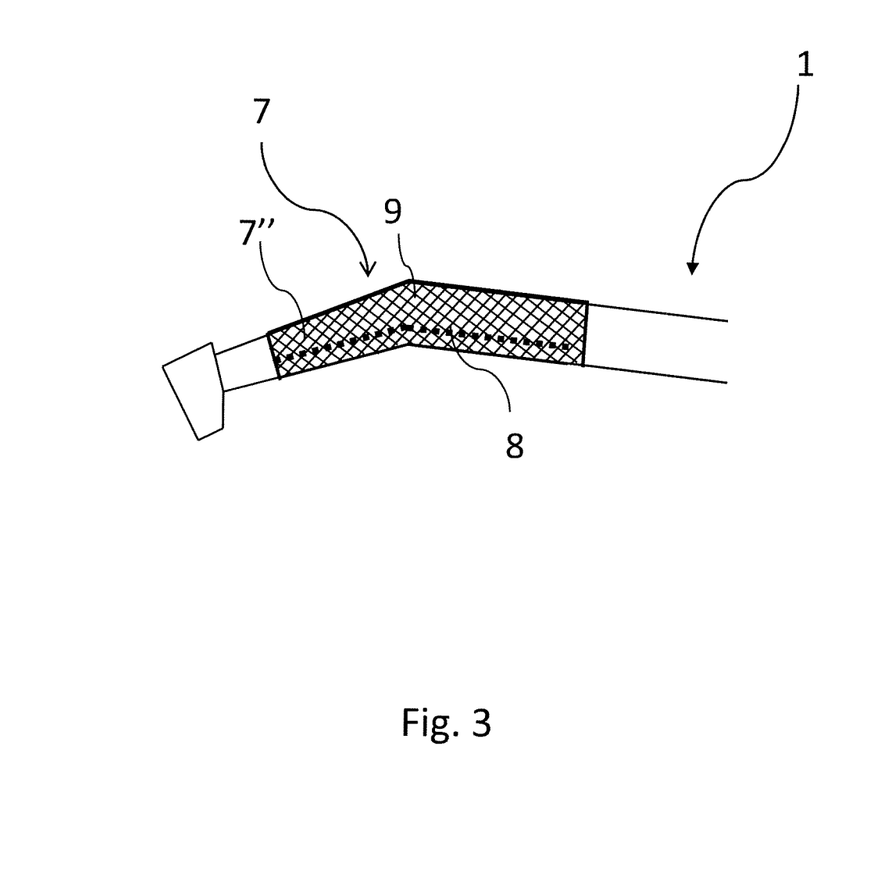
FIG. 3 is, similar to FIG. 2, a side view of a dental instrument, wherein the inventive elastic tubular element is in its unrolled state having a tight fit around the gripping area.

The gripping area 4 of the elongated element 3 of the instrument 1 can be shaped as a straight elongated element 3, or it can comprise one or more bends or angels and/or a cross sectional circumferential distance that varies in the longitudinal direction of the elongated gripping area 4. The elongated element 3 in FIGS. 1, 2 and 3 comprises a bend and a circumferential distance that increases in its longitudinal direction between the head element 2 and the bend.

The circumferential distance of the elongated element 3 can thus be smaller at one end compare to the other end. The open tubular element 7 can also have a varying circumferential distance along its longitudinal length, wherein for example the circumferential distance is smaller at the one longitudinal end compared the other, thereby increasing its circumferential distance in its longitudinal length. Since the open tubular element 7 is elastic, it is able to surround the gripping area in a tight fit manner onto the gripping area 4 as long as the gripping area 4 has cross sectional circumferential distances that are equal to or larger than the cross sectional circumferential distance of the tubular element 7 in its relaxed state.

The circumferential distance of the tubular element 7 can therefore be customized to fit with the circumferential distance of the gripping area 4 which it will be attached to.

The open tubular element 7 according to one aspect of the invention may comprise a tactile pattern to improve the grip compared to a smooth surface. The tactile pattern can be of any texture which improves the grip, such as for example consecutive lines, dots or any other geometrical shapes. The tactile patter should cover at least a part of the surface of the tubular element 7, preferably the entire surface.

The tubular element 7 is made of any kind of expandable and contractible elastic material such as a natural or synthetic rubber, thus enabling the material of the tubular element to expand when forcing the head of the instrument through the tubular elements inner diameter, and thereafter to contract when the tubular element is placed at the onset 5 of the gripping area. Further, the material may expand or contract when unrolled onto the gripping area depending on the circumferential distance of the gripping area. Examples of elastic materials which can be used are polychloroprene (neoprene), silicone, silicone rubber, acrylonitrile butadiene (nitrile), latex, polyisoprene, polyethylene, latex, polyurethane, and mixtures thereof.

The thickness of the wall of the open tubular element in its relaxed state is preferably at least 0.05 mm thick, even more preferably at least 0.1 mm thick, even more preferably at least 0.2 mm thick.

The elastic material may have a hardness in the range from 0 to 90 Shore A Durometer, preferably from 14 to 60 Shore A Durometer, and even more preferably from 20 to 55 Shore A Durometer, and the elastic material should easily expand and contract radially to accommodate various diameters of the instruments 1 without breaking or tearing apart during application or during use. The material should make a tight fit at least around the gripping area of the instrument 1.

For a detailed description of the measurement unit Shore A Durometer, see NON-PATENT DOCUMENT 1 and NON-PATENT DOCUMENT 2.

Shore A is an industrial standard for measuring hardness of solid rubber.

According to a further aspect of the invention, the tubular element 7 comprises at least one weakened area 8 extending along the entire longitudinal length of the tubular element 7.

The weakened area 8 will make it easier to remove the tubular element 7 after use compared to a tubular element 7 without such weakened area 8. The weakened area 8 may comprise perforations and/or a thinner elastic tubular material compared to the remaining part of the tubular element 7. Alternatively, or in addition, to such a weakened area, the material of tubular element 7 should be easily tearable by the user of the instrument without the need of external tools.

The tubular element 7 may also comprise an extruding flange/ear piece 9 placed at at least one of the longitudinal ends of the tubular element 7. The flange 9 is arranged in order to be easily grabbed by the user for tearing off the tubular element 7 from the instrument 1 after use.

The weakened area 8 can have any kind of configuration that will ease the removal of the tubular element 7 after use. For example, the tubular element 7 may comprise two weakened areas 8 along the longitudinal length of the tubular element 7 in form of repeated perforations. Further, the flange 9 can be positioned at one of the longitudinal ends of the tubular element 7. By lifting the flange 9 and dragging it in the longitudinal direction of the tubular element 7, the weakened areas 8 will tear the tubular element 7 apart, thereby removing the tubular element 7 with ease from the instrument 1.

The open tubular element 7 according to the invention should be prepacked in a sterilized container before use, and it should be packed in its rolled-up state.

The invention also discloses a medical instrument 1 wherein the open tubular element 7 is attached thereto. The medical instrument 1 comprises an elongated element 3 having a gripping area 4, and a head element 2 which is attached to one of the ends of the elongated element 3. The open tubular element 7 is attached to at least the gripping area 4 of the dental instrument 1.

Further, invention concerns a method for attaching the open tubular element 7 of the elastic material around the gripping area 4 of the elongated instrument 1. The tubular element 7 is open in both longitudinal ends. The elongated instrument 1 comprises an elongated element 3 having an elongated gripping area 4 and a head element 2 being attached to one of the ends of the elongated element 3, see FIG. 1. The method comprises forcing the head element 2 through the tubular element 7 while the tubular element 7 is in the rolled up state 7'. The tubular element 7 in its rolled up state 7' is thereafter placed around the onset 5 of the gripping area 4, see FIG. 2. The tubular element 7 is then unrolled to an unrolled state 7" around the longitudinal length of at least the gripping area 4, resulting in a tight fit around the elongated element 3, see FIG. 3.

It should be understood by the person skilled in the art that the tubular element 7 can be unrolled in both longitudinal directions of the instruments 1, depending on which way the rolled up tubular element 7 is placed around the onset 5 of the gripping area 4. Thus, the tubular element 7 can be placed in its rolled up state 7' around the onset 6 of the gripping area 4. The tubular element 7 is then unrolled along the longitudinal length of at least the gripping area 4, resulting in tight fit around the elongated element 3. In which longitudinal direction the tubular element 7 is being unrolled depends on which direction the tubular element 7 is applied onto.

The tubular element 7 should not, due to the tight fit configuration, be able to slide after being unrolled. The stable, non-sliding, condition is achieved due to frictional engagement between the instrument 1 and the tubular element 7. Consequently, the risk that the tubular element slips out of the instrument 1 is reduced to nil or insignificant.

To further ensure such tight fit configuration the tubular element 7 can be strengthened in both longitudinal ends wherein the ends are thicker than the thickness of the remaining part of the tubular element.

EXAMPLE

A dental instrument 1 having a head element 2 with a circumferential distance, $d_{head}$, of 15 mm is forced through the inner opening of a tubular element 7 of neoprene having a circumferential distance in its relaxed state of 9 mm. In its relaxed state the thickness of the tubular wall is 0.25 mm. The tubular element 7 is expanding its circumferential distance as the head element 2 of the instrument 1 is forced through the inner opening of the tubular element 7. The tubular element 7 is thus expanding to a circumferential distance of at least 15 mm. Thereafter, the tubular element 7 is placed onto the onset 5 of the gripping area of the shaft of the instrument 1, the onset 5 having a circumferential distance, $d_{grip}$, of 11 mm Thereafter the tubular element 7 is unrolled onto the gripping area 4 of the instrument 1, establishing a tight fit thereto.

FIG. 4 illustrates a part of a prior art dental instrument 1 to which the grip device according to the present invention can be attached. The instrument is normally made of a metal such as stainless steel. The head 2 of the instrument 1 has in this specific embodiment shown in FIG. 4 a larger maximum diameter, $d_{head}$, when compared to the maximum diameter, $d_{grip}$, of the gripping area 4.

In the preceding description, various aspects of the gripping device and the medical instrument according to the invention have been described with reference to the illustrative embodiment. For purposes of explanation, specific numbers, systems and configurations were set forth in order to provide a thorough understanding of the grip device, the medical instrument and its workings. However, this description is not intended to be construed in a limiting sense. Various modifications and variations of the illustrative embodiment, as well as other embodiments of the disclosed devices, which are apparent to persons skilled in the art to which the disclosed subject matter pertains, are deemed to lie within the scope of the present invention.

The invention claimed is:

1. A dental instrument comprising:
   an elongated medical instrument comprising an elongated element, the elongated element of the elongated medical instrument having a gripping area and a head element being attached to an end of the elongated element; and
   a medical instrument grip device for the elongated medical instrument, the medical instrument grip device comprising an open tubular element of elastic material;
   wherein the tubular element is open in both longitudinal ends and is configured to switch between a rolled up state and a fully unrolled state,
   wherein the tubular element is further configured such that the head element of the elongated element may be forced through an inner opening of the tubular element when the tubular element is stretched and in the rolled up state, and to create a tight fit around the gripping area of the elongated element when the tubular element is in the fully unrolled state,
   wherein a cross sectional circumferential distance of the tubular element before stretching is equal or smaller than cross sectional circumferential distances of the gripping area of the elongated element onto which the tubular element is to be fitted,
   wherein a ratio between the circumferential distance of the tubular element before stretching and the circumferential distance of the tubular element after reaching a stretched expanded state when forcing the head element of the elongated element through the inner opening, is between 1:1.1 and 1:5,
   wherein the material is chosen such that the tubular element has an ability to contract back to a relaxed state, or at least contract enough to allow the tubular element to make a tight fit on to the gripping area of the elongated element, and
   wherein the circumferential distance of an onset of the gripping area of the elongated element, $d_{grip}$, is smaller than the circumferential distance of the head element of the elongated element, $d_{head}$.

2. The dental instrument according to claim 1, wherein an outer surface of the tubular element comprises a tactile pattern.

3. The dental instrument according to claim 1, wherein the elastic material is selected from one of polychloroprene (neoprene), silicone, silicone rubber, acrylonitrile butadiene (nitrile), latex, polyisoprene, polyethylene, latex, polyurethane and mixtures thereof.

4. The dental instrument according to claim 1, wherein the open tubular element comprises a smaller circumference at a first longitudinal end compared to a second longitudinal end, thereby expanding the circumference of the material from the first longitudinal end to the second longitudinal end.

5. The dental instrument according to claim 1, comprising at least one weakened area along a longitudinal length of the tubular element.

6. The dental instrument according to claim 5, wherein the weakened area comprises perforations.

7. The dental instrument according to claim 5, wherein a thickness of the weakened area is thinner than a thickness of a remaining part of the tubular element.

8. The dental instrument according to claim 1, wherein the tubular element is tearable by a user of the dental instrument without need of external tools.

9. The dental instrument according to claim 1, wherein the tubular element comprises an extruding flange at an end of the tubular element.

10. A method for attaching a medical instrument grip device in form of a tubular element around a gripping area of an elongated element of an elongated medical instrument,
wherein the tubular element is open in both longitudinal ends and made of an elastic material,
wherein the elongated element of the elongated instrument further comprises a head element being attached to an end of the elongated element,
wherein a cross sectional circumferential distance of the tubular element before stretching is equal or smaller than cross sectional circumferential distances of the gripping area of the elongated element onto which the tubular element is to be fitted,
wherein a ratio between the circumferential distance of the tubular element before stretching and the circumferential distance of the tubular element after reaching a stretched expanded state when forcing the head element of the elongated element through an inner opening of the tubular element, is between 1:1.1 and 1:5,
wherein the method comprises:
forcing the head element of the elongated element through the inner opening of the stretched tubular element, the tubular element being in a rolled up state,
placing the rolled up tubular element around an onset of the gripping area of the elongated element, and
unrolling the tubular element around a longitudinal length of at least the gripping area of the elongated element, and
wherein the material of the tubular element is chosen such that the tubular element has an ability to contract back to a relaxed state, or at least contract enough to allow the tubular element to make a tight fit on to the gripping area of the elongated element.

11. The method according to claim 10, wherein an outer surface of the tubular element comprises a tactile pattern.

12. The method according to claim 10, wherein the elastic material is selected from one of polychloroprene (neoprene), silicone, silicone rubber, acrylonitrile butadiene (nitrile), latex, polyisoprene, polyethylene, latex, polyurethane and mixtures thereof.

13. The method according to claim 10, wherein the open tubular element comprises a smaller circumference at a first longitudinal end compared to a second longitudinal end, thereby expanding the circumference of the material from the first longitudinal end to the second longitudinal end.

14. The method according to claim 10, comprising at least one weakened area along a longitudinal length of the tubular element.

15. The method according to claim 14, wherein the weakened area comprises perforations.

16. The method according to claim 14, wherein a thickness of the weakened area is thinner than a thickness of a remaining part of the tubular element.

17. The method according to claim 10, wherein the tubular element is tearable by a user of the elongated medical instrument without need of external tools.

18. The method according to claim 10, wherein the tubular element comprises an extruding flange at an end of the tubular element.

19. The method according to claim 10, wherein the medical instrument grip device for an elongated medical instrument, said elongated medical instrument comprising an elongated element having a gripping area and a head element being attached to an end of the elongated element, the medical instrument grip device consisting of:
an open tubular element of elastic material;
wherein the tubular element is open in both longitudinal ends and is configured to switch between a rolled up state and a fully unrolled state,
wherein the tubular element is further configured such that the head element of the elongated element may be forced through an inner opening of the tubular element when the tubular element is stretched and in the rolled up state, and to create a tight fit around the gripping area of the elongated element when the tubular element is in the fully unrolled state,
wherein a cross sectional circumferential distance of the tubular element before stretching is equal or smaller than cross sectional circumferential distances of the gripping area of the elongated element onto which the tubular element is to be fitted,
wherein a ratio between the circumferential distance of the tubular element before stretching and the circumferential distance of the tubular element after reaching a stretched expanded state when forcing the head element of the elongated element through the inner opening, is between 1:1.1 and 1:5, and
wherein the material is chosen such that the tubular element has an ability to contract back to a relaxed state, or at least contract enough to allow the tubular element to make a tight fit on to the gripping area of the elongated element.

* * * * *